US008545545B2

(12) United States Patent
Shanley et al.

(10) Patent No.: US 8,545,545 B2
(45) Date of Patent: Oct. 1, 2013

(54) STENT WITH FLEXIBLE HINGES

(75) Inventors: John F. Shanley, Redwood City, CA (US); Prasanna Venkatesh Muralidharan, Menlo Park, CA (US)

(73) Assignee: Innovational Holdings LLC, New Brunswick, NJ (US)

( * ) Notice: Subject to any disclaimer, the term of this patent is extended or adjusted under 35 U.S.C. 154(b) by 1258 days.

(21) Appl. No.: 11/582,818

(22) Filed: Oct. 18, 2006

(65) Prior Publication Data

US 2008/0097579 A1  Apr. 24, 2008

(51) Int. Cl.
 *A61F 2/82* (2013.01)
(52) U.S. Cl.
 USPC ......................... 623/1.15; 623/1.42
(58) Field of Classification Search
 CPC ..................... A61F 2/82; A61F 2/91
 USPC ..................... 623/1.15, 1.42, 1.43
 See application file for complete search history.

(56) References Cited

U.S. PATENT DOCUMENTS

| | | | |
|---|---|---|---|
| 5,776,181 A | 7/1998 | Lee et al. | |
| 5,810,872 A | 9/1998 | Kanesaka et al. | |
| 5,922,020 A * | 7/1999 | Klein et al. | 623/1.15 |
| 6,241,762 B1 | 6/2001 | Shanley | |
| 6,245,101 B1 * | 6/2001 | Drasler et al. | 623/1.15 |
| 6,423,091 B1 | 7/2002 | Hojeibane | |
| 6,475,237 B2 | 11/2002 | Drasler et al. | |
| 6,506,437 B1 * | 1/2003 | Harish et al. | 427/2.25 |
| 6,764,507 B2 | 7/2004 | Shanley et al. | |
| 7,060,093 B2 * | 6/2006 | Dang et al. | 623/1.42 |
| 2001/0027339 A1 * | 10/2001 | Boatman et al. | 623/1.15 |
| 2002/0068969 A1 | 6/2002 | Shanley et al. | |
| 2004/0034402 A1 | 2/2004 | Bales et al. | |
| 2004/0044401 A1 | 3/2004 | Bales et al. | |
| 2004/0093073 A1 * | 5/2004 | Lowe et al. | 623/1.15 |
| 2004/0149294 A1 * | 8/2004 | Gianchandani et al. | 128/879 |
| 2004/0172123 A1 | 9/2004 | Lootz et al. | |
| 2004/0220662 A1 * | 11/2004 | Dang et al. | 623/1.16 |
| 2007/0129786 A1 * | 6/2007 | Beach et al. | 623/1.15 |

FOREIGN PATENT DOCUMENTS

| | | |
|---|---|---|
| DE | 20019429 U | 3/2002 |
| WO | WO 00/24340 A | 5/2000 |
| WO | WO 01/58386 A1 | 8/2001 |
| WO | WO 03/015664 A1 | 2/2003 |
| WO | WO 2006/026782 A | 3/2006 |
| WO | WO 2006/029619 A1 | 3/2006 |

OTHER PUBLICATIONS

International Search Report dated Aug. 8, 2008 for application PCT/US2007/081732.

* cited by examiner

*Primary Examiner* — Jason-Dennis Stewart

(57) ABSTRACT

A helical stent includes at least one helical winding. Each helical winding includes a plurality of alternating long struts and short struts, ends of at least some of the long struts being joined to an end of an adjacent short strut by a flexible hinge arrangement, the struts being substantially rigid. The stent also includes at least one interconnection member connecting a hinge arrangement on one turn of the at least one winding with a hinge arrangement on an adjacent turn of the at least one winding. Fewer than all hinge arrangements on the at least one helical winding are connected to other hinge arrangements by an interconnection member.

12 Claims, 7 Drawing Sheets

STENT WITH FLEXIBLE HINGES

BACKGROUND AND SUMMARY

The present application relates to expandable stents and, more particularly, to expandable stents with flexible hinges.

It is desirable to provide flexibility in stents to facilitate introduction of the stent into vessels that are difficult to reach. Often, however, characteristics of the stent that provide longitudinal flexibility that is desirable when introducing the stent into the vessel can be disadvantageous in terms of keeping the stent in an expanded condition. For example, stents formed from interconnected rings with closed cell structures or generally diamond-shaped cells are typically less flexible than stents formed from one or more helices, but are usually more uniformly and consistently expandable than helical stents. It is desirable to provide a stent with substantial flexibility that is adapted to be expanded in a uniform and consistent fashion.

In WO 03/015664, which is incorporated by reference, a stent having interconnected struts with openings for drug delivery is disclosed. However, elements for bridging the struts are generally thinner and spaced further apart than the struts. Thus, for such drug-eluting stents, the bridging element can provide an area of reduced or less consistent drug delivery. It is desirable to provide a drug-eluting stent in which areas of reduced or less consistent drug delivery can be reduced.

In accordance with an aspect of the present invention, a helical stent comprises at least one helical winding, each helical winding comprising a plurality of alternating long struts and short struts, ends of at least some of the long struts being joined to an end of an adjacent short strut by a flexible hinge arrangement, the struts being substantially rigid, and at least one interconnection member connecting a hinge arrangement on one turn of the at least one winding with a hinge arrangement on an adjacent turn of the at least one winding, wherein fewer than all hinge arrangements on the at least one helical winding are connected to other hinge arrangements by an interconnection member.

In accordance with another aspect of the present invention, a helical stent comprises at least one helical winding, each helical winding comprising a plurality of struts, ends of the struts being joined to an end of an adjacent strut by a flexible hinge arrangement, the struts being substantially rigid, and at least one interconnection member connecting a hinge arrangement on one turn of the at least one winding with a hinge arrangement on an adjacent turn of the at least one winding, wherein fewer than all hinge arrangements on the at least one helical winding are connected to other hinge arrangements by an interconnection member.

In accordance with another aspect of the present invention, a helical stent comprises at least one helical winding, each helical winding comprising a plurality of pairs of long struts and short struts, the struts being substantially rigid, and a plurality of flexible hinge arrangements, ends of at least some of the long struts being joined to an end of an adjacent short strut by the hinge arrangements, each of the plurality of flexible hinge arrangements comprising a substantially rigid connecting member and a first flexible hinge between the connecting member and a long strut and a second flexible hinge between the connecting member and a short strut.

In accordance with another aspect of the present invention, a helical stent comprises at least one helical winding, each helical winding comprising a plurality of pairs of long strut assemblies and short strut assemblies, the struts being substantially rigid, the long strut assembly comprising at least two struts and being longer than the short strut assembly, and a plurality of flexible hinge arrangements, ends of at least some of the long strut assemblies being joined to an end of an adjacent short strut assembly by the hinge arrangements, each of the plurality of flexible hinge arrangements comprising a substantially rigid connecting member and a first flexible hinge between the connecting member and a long strut assembly and a second flexible hinge between the connecting member and a short strut assembly.

In accordance with another aspect of the present invention, an expandable stent includes a plurality of expandable cells having at least eight sides and formed by a plurality of alternating long and short, substantially non-deforming struts interconnected by deformable hinges.

In accordance with a further aspect of the present invention, an expandable stent includes a plurality of struts extending substantially longitudinally along an axis of the stent in an unexpanded configuration and a plurality of hinges interconnecting the struts. The plurality of hinges each have a straight active portion which extends substantially circumferentially around the stent in the unexpanded configuration and two curved portions interconnecting the active portion to adjacent ones of the plurality of struts.

In accordance with another further aspect of the present invention, an expandable stent includes a plurality of struts extending substantially longitudinally along an axis of the stent in an unexpanded configuration and a plurality of hinge arrangements interconnecting the struts. Each of the hinge arrangements includes a central portion and four tapered hinges each connected at one end to the central portion and at another end to one of the plurality of struts. Each of the tapered hinges has a smallest width closer to the struts and a largest width closer to the central portion.

In accordance with another aspect of the present invention, an expandable stent includes a plurality of struts extending substantially longitudinally along an axis of the stent in an unexpanded configuration, a plurality of first hinges interconnecting the struts, and a plurality of interconnecting hinge arrangements interconnecting the struts. The plurality of hinges each have a straight active portion which extends substantially circumferentially around the stent in the unexpanded configuration interconnected to adjacent ones of the plurality of struts. Each of the interconnecting hinge arrangements includes a central portion and four second hinges each connected at one end to the central portion and at another end to one of the plurality of struts.

BRIEF DESCRIPTION OF THE DRAWINGS

The features and advantages of the present invention are well understood by reading the following detailed description in conjunction with the drawings in which like numerals indicate similar elements and in which.

DETAILED DESCRIPTION

Figure 1:
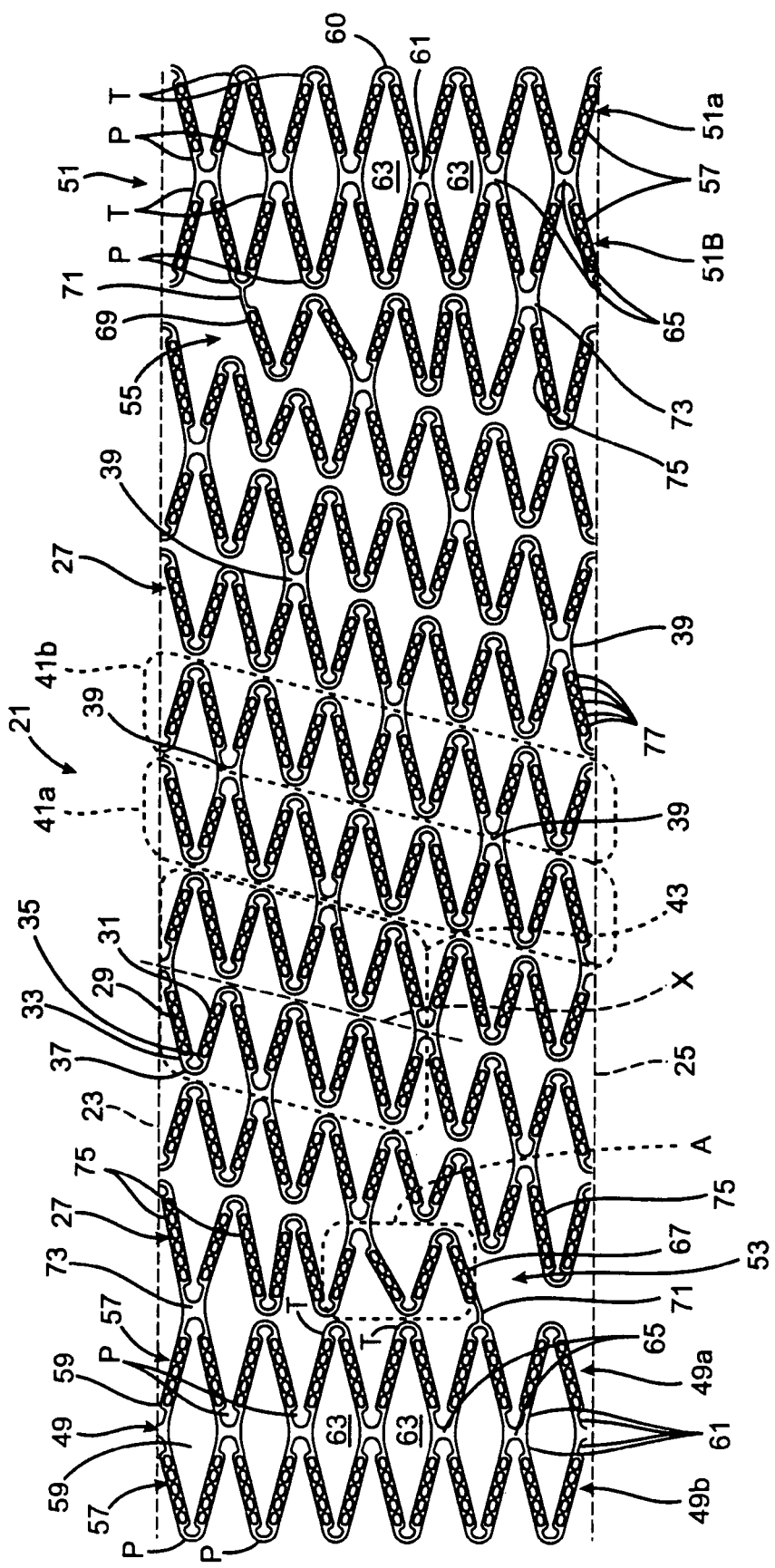
FIG. 1 is a view of a stent according to an embodiment of the present invention shown in partly expanded form, cut along a line parallel to a longitudinal axis of the stent, and unrolled.
Figure 2A:
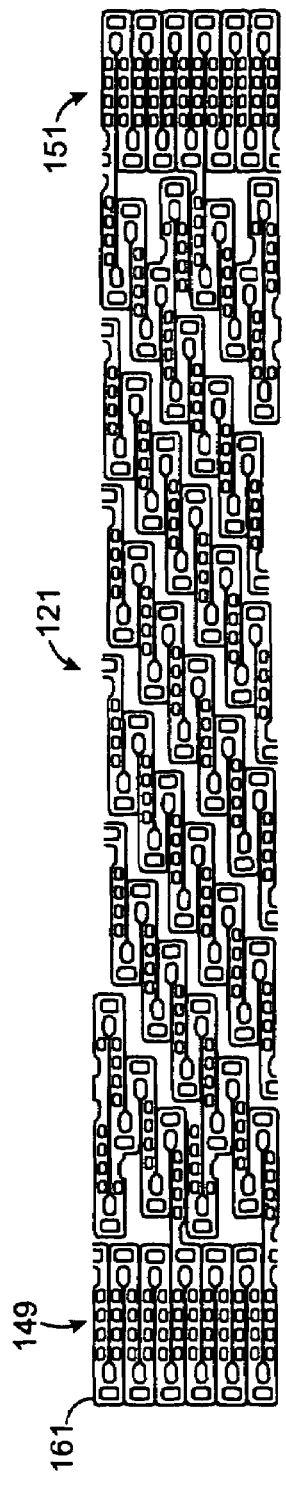
FIGS. 2A and 2B are views of a stent according to another embodiment of the present invention shown in unexpanded and expanded form, cut along a line parallel to a longitudinal axis of the stent, and unrolled.
Figure 2B:
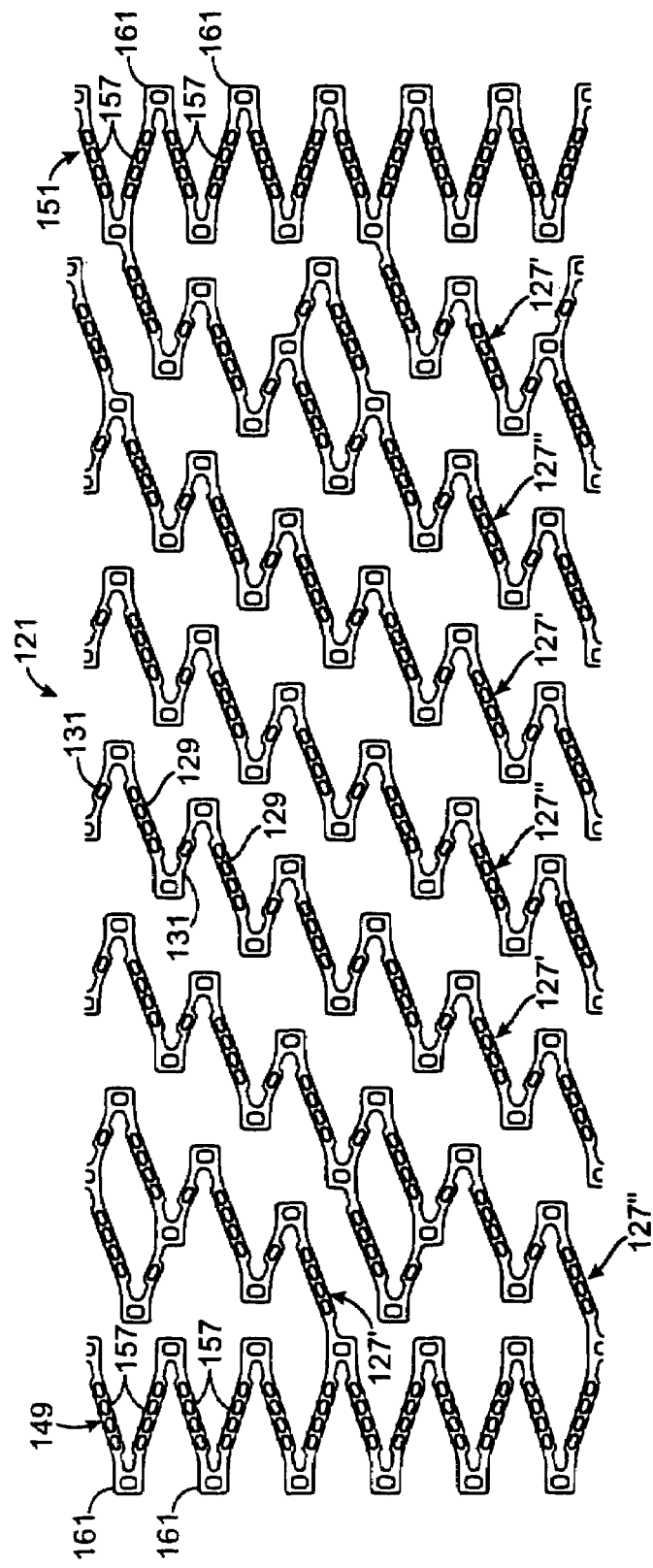

A helical stent 21 according to an embodiment of the present invention is shown in FIG. 1. The stent 21 is shown in FIG. 1 as it would appear if the stent were in an at least partially expanded condition and cut along its length. More particularly, the stent 21 shown in FIG. 1 is shown in the form in which it would appear if it were cut along its length and the cut article was laid out flat. The stent 21 can be formed in any suitable manner, such as by being laser cut from a tube made of a suitable material including cobalt chromium alloys, stainless steel alloys or nickel titanium alloys. In an "as cut" version of the stent 21, top and bottom edges 23 and 25 would ordinarily be joined together. FIGS. 2A and 2B show another embodiment of a stent 121 in an unexpanded and an at least partially expanded condition, respectively, and cut along its length. The present invention will be described as a vascular stent, such as a coronary or peripheral stent. However, the stent structure described can also take the form of other known stents. In practice, while a laser cut tubular coronary stent might have a diameter of approximately 2 mm when it is cut from a metal tube, it is ordinarily subsequently crimped to a more compressed condition (such as is shown in FIG. 2A), to, for example, a diameter of approximately 1 mm and, upon expansion, such as by a balloon catheter, the expanded stent might have a diameter of approximately 2-4 mm, i.e., the components of the "expanded" stent would be more expanded than they appear in the illustrated "as cut" version. Other types of stents would have other diameters corresponding to their application.

The stent 21 includes at least one helical winding 27. The stent 21 in FIG. 1 includes one helical winding 27. The stent 121 shown in FIG. 2B and the stent 221 shown in FIG. 3 each include two helical windings 127' and 127", and 227' and 227", respectively. If desired, the stent can have more than two helical windings. Ordinarily, each helical winding 27 will have multiple winding turns, usually at least three turns.

As seen, for example, in FIG. 1, each helical winding 27 comprises a plurality of alternating long struts 29 and short struts 31. Ends 33 of at least some of the long struts 29 are joined to an end 35 of an adjacent short strut 31 by a flexible hinge arrangement 37. The struts 29 and 31 are substantially rigid compared to the hinge arrangement 37 and ordinarily do not substantially bend or deform during expansion of the stent 21 from an unexpanded condition to an expanded condition. The hinge arrangements 37 account for substantially all deformation or bending of components of the stent 21. During expansion of the stent from an unexpanded condition to an open or expanded condition, substantially all deformation occurs in the hinge arrangements, which are designed to facilitate uniform and consistent expansion of the stent, and which can facilitate retaining the stent in an expanded condition. Stents with ductile hinges connecting more rigid components such as struts are disclosed in U.S. Pat. No. 6,241,762, which is incorporated by reference.

Periodically, the alternating pattern of long and short struts 29 and 31 connected by hinge arrangements is interrupted by an interconnection hinge arrangement 39. The interconnection hinge arrangement 39 connects one turn 41a of the at least one winding 27 with an adjacent turn 41b of the at least one winding. Fewer than all bends of the winding 27 are connected to other bends by an interconnection hinge arrangement 39. The interconnection hinge arrangements 39 have a rigid central portion and four deformable hinge portions connecting to four adjacent struts (two short and two long struts).

Ordinarily, a plurality of interconnection hinge arrangements 39, i.e., at least two, are provided. Each interconnection hinge arrangement 39 replaces the hinge arrangement 37 on one turn 41a of the at least one winding 27 and the hinge arrangement on the adjacent turn 41b of the at least one winding. In this way, two successive (in the direction of the helix) interconnection hinge arrangements 39 delimit a cell 43 defined by long and short struts 29 and 31 and hinge arrangements 37 between the successive interconnection members.

Ordinarily, the long and short struts 29 and 31 are substantially straight, although they can be other shapes, such as curved, etc. When the struts are substantially straight, as can be seen in FIG. 1, the cell 43 can be multi-sided. FIG. 1 shows a cell with 16 sides (hexadecahedron) formed by 8 short and 8 long struts, however, cells with different numbers of sides can be provided (e.g., 4, 8, 12, 16, 20 . . . ). By linking only some of the bends with interconnections 39 between adjacent turns 41a and 41b of the helical winding 27, i.e., by providing fewer interconnections than pairs of hinge arrangements, the stent 21 can have substantial flexibility, while retaining even coverage upon expansion.

Figure 4A:
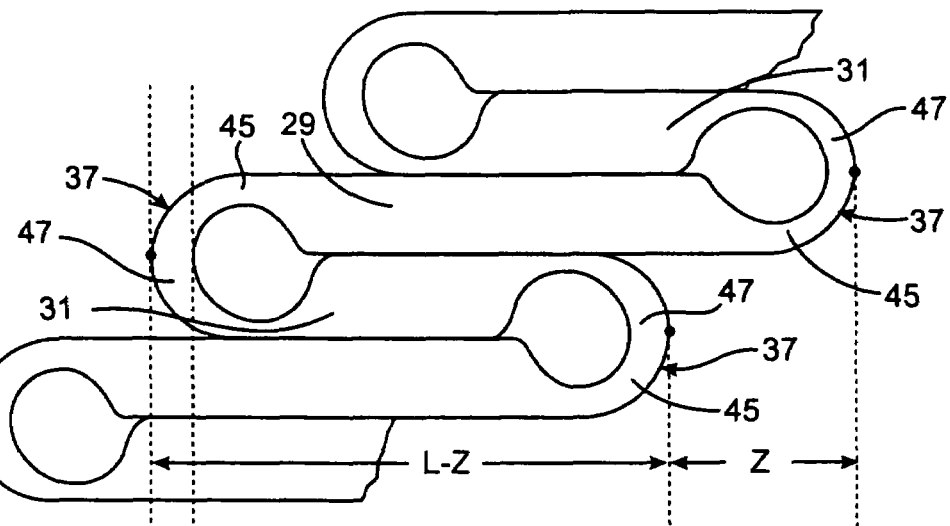
FIGS. 4A and 4B are views of a portion of a stent according to an embodiment of the present invention shown in unexpanded and expanded form.
Figure 4B:
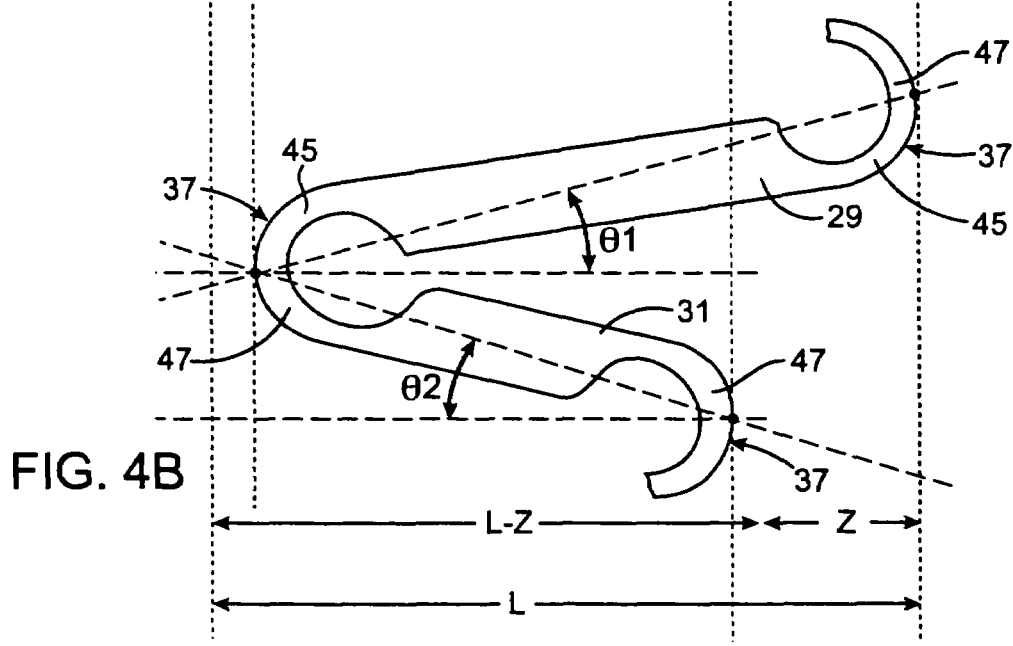

As seen in FIGS. 4A and 4B, the hinge arrangement 37 can comprise a first portion 45 connected to a long strut 29 and a second portion 47 connected to an adjacent short strut 31. The first portion 45 and the second portion 47 can have different cross-sectional shapes or other structural or other differences. For example, the second portion 47 of the hinge arrangement 37 can be provided with a smaller cross-sectional shape than the first portion 45 of the hinge arrangement, which can tend to make it easier to bend the second portion of the hinge arrangement. By providing an appropriate combination of characteristics for the first and second portions 45 and 47 of the hinge assembly 37, characteristics of the stent during expansion from an unexpanded condition to an expanded condition can be controlled. For example, the stent shown in FIGS. 1, 2A and 2B are approximately the same length in the unexpanded position as in the open position. In other words, the stent does not significantly shorten upon expansion. In FIG. 2A, it will be seen that the overall length of the stent 121 is largely a function of the lengths of the struts 129 and 131 in the longitudinal direction of the stent. In FIG. 2A, it will be seen that the overall length of the stent 121 is largely a function of the lengths of those same struts 129 and 131, as well as a function of the angle with which those struts 129 and 131 make with the longitudinal axis of the stent.

FIGS. 4A and 4B show a single pair of adjacent long and short struts 29 and 31 in a closed and an open position, respectively. It will be seen that the combined length of a long and a short strut and is equal to "L" when they lie substantially along the axis of the stent in the closed state, where the long strut's length is equal to "L" and the short strut's length is equal to "L-Z", and the long strut completely overlaps the short strut. For each zig-zag of such a strut pair along the helical winding, the helix will advance a length "Z". If the stent is opened such that, as in FIG. 4B the long strut forms an angle of Θ1 with the longitudinal axis of the stent, it's length along the axis will be equal to Lcos (Θ1), which will be shorter than the length L. However, if the component of the short strut's 31 length along the longitudinal axis is shorter by the same amount, the helix will still advance a length "Z" for each zig-zag. This can be accomplished, for example, where the short strut 31 forms a certain angle Θ2 with the longitudinal axis greater than the angle Θ1 formed by the long strut 29.

Cells 43 in FIG. 1 defined by connected long and short struts 29 and 31 have long axes x that are skewed or at an angle with respect to a circumference of the generally cylindrical stent. Axes of individual, generally diamond shaped portions of a cell extending from hinge to hinge can extend generally parallel to the axis of the stent.

As seen in FIG. 1, the stent 21 can comprise first and second flexible end rings 49 and 51 hingedly joined to opposite ends 53 and 55, respectively, of the at least one helical winding 27. The end rings 49 and 51 can take a variety of suitable shapes. In the embodiment of FIG. 1, each end ring 49 and 51 can comprise two ring halves 49a and 49b, and 51a and 51b. Each ring half can comprise a plurality of end ring struts 57 joined to each other at ends 59 thereof by flexible end ring hinge arrangements 60 and interconnecting hinge arrangements 61 that define alternating left- and right-pointing bends, which may be in the form of gentle, round curves, or sharper, more angular curves, in a zig-zag or accordion fashion.

If each left-pointing bend to left-pointing bend or right-pointing bend to right-pointing bend "wave" is considered as defining 360°, then the two ring halves 49a and 49b and 51a and 51b of each ring 49 and 51 are 180° out of phase with each other and joined by interconnection hinge arrangements 61 to define a plurality of diamond shaped end ring cells 63. The interconnection hinge arrangements 61 include a rigid central portion 65 and four hinges like the interconnection hinge arrangements 39 and may be substantially identical to them.

In the embodiment of FIG. 1, all of the left-pointing bends of the first end ring halves 49a and 51a are joined to corresponding right-pointing bends of the second end ring halves 49b and 51b to form the closed diamond shaped cells 63. Although in this embodiment, the end ring struts 57 are substantially straight and the cells 63 are substantially diamond-shaped. However, other arrangements, including open cell configurations such as where every other pair of left-pointing bends are attached, can be provided.

The long and short struts 29 and 31 and the flexible hinge arrangements 37 of the at least one helical winding 27 typically also define alternating left-pointing bends P and right-pointing bends T. An end strut 67 at the first end 53 of the helical winding 27 can be disposed at a left-pointing bend and can be connected to an end ring hinge arrangement 61 at a right-pointing bend of the first end ring half 49a of the first end ring 49. Similarly, an end strut 69 at the second end 55 of the helical winding 27 can be disposed at a right-pointing bend and can be connected to an end ring hinge arrangement 61 at a left-pointing bend of the second end ring half 51b of the second end ring 51. The end struts 67 and 69 at the first and second ends 53 and 55 of the helical winding 27 can be connected to the end ring hinge arrangement 60 at the right-pointing bend of the first end ring half 49a of the first end ring 49 and at the left-pointing bend of the second end ring half 51b of the second end ring 51, respectively, by a flexible end hinge arrangement 71. This provides for freedom of motion of the end strut for expansion while maintaining even strut distribution on expansion.

For at least some of the alternating left-pointing bends and right-pointing bends of a helical winding 27, in a center portion of the stent, all the short struts are of the same length and all the long struts are of the same length. By contrast, in some parts of the helical winding such as the ends of the helical winding as seen at "A" in FIG. 1, the strut lengths are varied according to the available space and to achieve uniformity of strut coverage after expansion. Often, as seen in FIGS. 1 and 3, but not always, several strut pairs in a row will have struts of the same length.

In addition to or instead of connecting the winding 27 to the end rings 49 and 51 by the end hinge arrangements 71 at ends 53 and 55 of the winding, at least one interconnection hinge arrangement 73 can be used. As seen in FIG. 1, the first right-pointing bend at which the flexible end hinge arrangement 71 joins the end strut 67 of the winding 27 to the first end ring 49 and the second right-pointing bend at which the interconnection hinge arrangement 73 joins the winding to the first end ring can be non-successive, which can enhance flexibility of the stent 21. The interconnections 73 typically include a rigid portion of four hinges like the interconnections 39 and may be substantially identical to them.

Figure 3:
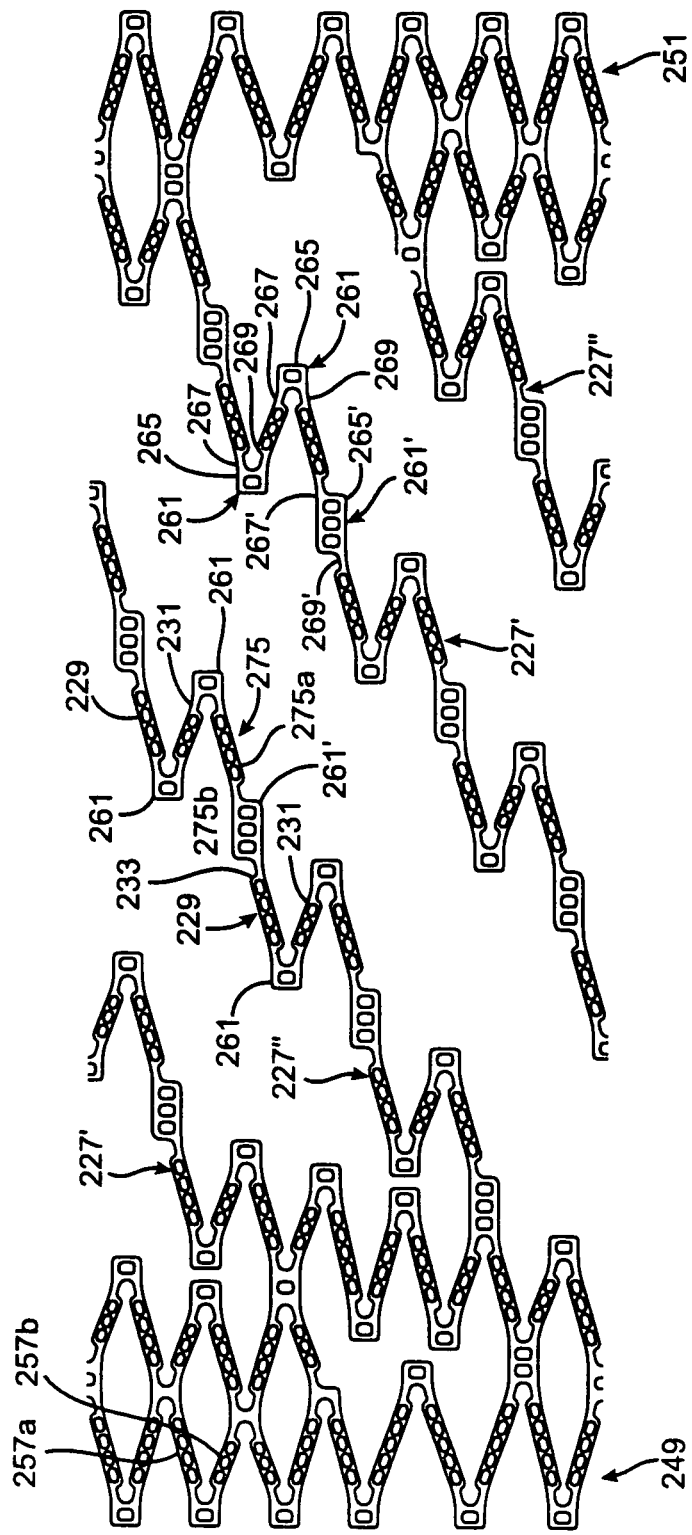
FIG. 3 is a view of a stent according to another embodiment of the present invention shown in partly expanded form, cut along a line parallel to a longitudinal axis of the stent, and unrolled.
Figure 5:
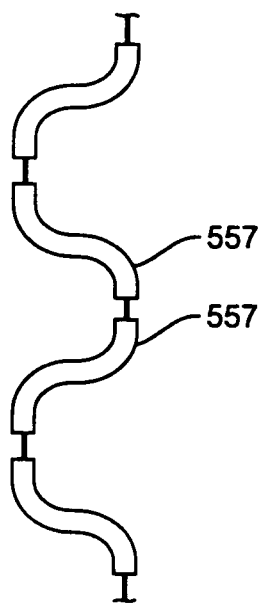
FIG. 5 is a schematic view of a portion of an end ring for a stent according to an embodiment of the present invention.

FIGS. 2A-2B and FIG. 3 show other forms of end-rings 149 and 151, and 249 and 251, respectively, than of the type shown in FIG. 1. Referring to FIG. 2B, in the end rings 149 and 151, each end ring comprises a plurality of end ring struts 157 joined to each other at ends thereof by flexible end ring hinge arrangements 161 that define alternating left-pointing bends and right-pointing bends. There are not two end ring halves, as in the embodiment of FIG. 1. The end rings 149, 151, 249, and 251 can otherwise be similar to the end rings 49 and 51, particularly in terms of how they are connected to the helical winding(s) of the stent. In FIGS. 2A-2B, the end ring struts 157 are shown as substantially straight struts such that, when the stent is in the expanded state (FIG. 2B), the end ring struts 157 and hinge arrangements 161 define a substantial Z-shape. As seen in FIG. 5, if the end ring struts 557 are some other shape, such as curved or S-shaped, other shapes can be formed, such as substantial S-shapes, upon expansion of the stent.

The end-rings 249 and 251 of FIG. 3 include a combination of diamond shaped portions and z-shaped portions. Additionally, while the end ring struts 57 in the embodiment of FIG. 1, as well as the end ring struts 157 in FIG. 2B, are all the same length, it is not necessary that they be the same length and, as seen in FIG. 3, some end ring struts 257a may be longer than other end ring struts 257b.

Referring again to FIG. 1, while the helical winding 27 can have alternating long and short struts 29 and 31 along its entire length, it may be desirable to provide additional struts 75 having lengths other than the lengths of the long and short struts, particularly in the area of the transition from the end rings 49 and 51 to the helical winding toward the ends 53 and 55 of the winding. These additional, transitional struts 75 may be at the ends 53 and 55, or near the ends, and are sized to ensure, inter alia, substantially even stent coverage while preventing overlap between a left-pointing bend of a series of zig-zag struts of the winding 27 and a right-pointing bend of a series of zig-zag struts of an end ring.

The helix is formed with an odd number of struts in each 360 degree turn of the helix which results in a configuration in which the hinge arrangements 39 are lined up with hinge arrangements in adjacent turns. This is sometimes called an 180 degree out of phase construction.

Some or all of the struts 29, 31, 57, and 75 can comprise at least one opening 77 for receiving a drug. WO 03/015664, which is incorporated by reference, describes a non-coated drug-eluting stent with openings for receiving a drug. In addition to having openings 77 in the struts 29, 31, 57, and 75, openings for drugs can be provided in the interconnection 39, in the end ring interconnection 65, in the end interconnection 73, in the hinge arrangement (see, for example, openings 77 in the rigid portions of the hinge assemblies 137 and 237 in FIGS. 2A-2B and 3). Although the examples of stents shown herein include openings for beneficial agents, these openings and the beneficial agents may be omitted. Where the openings are omitted, an agent may be incorporated into the stent in other ways, such as a coating or a polymer stent containing drug.

The stent 21 can be configured with left-pointing bends and right-pointing bends of strut pairs of struts 29 and 31 on successive turns of the helical winding 27 being relatively close to each other such that, although an interconnection member 39 with a drug opening 77 may not be disposed between each left-pointing bend and right-pointing bend, drug delivery from openings on the stent will be substantially consistent, i.e., there are no particularly large spaces between drug openings.

Figure 6:
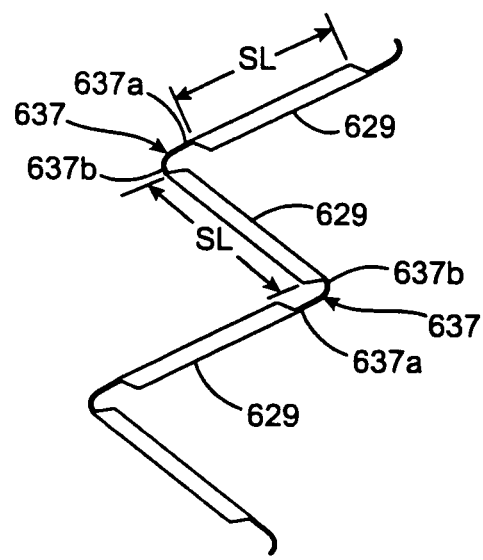
FIG. 6 is a schematic view of a portion of a helical winding according to another embodiment of the present invention.

The helical stent according to the present invention will ordinarily, as in the embodiment of FIG. 1, comprise a plurality of alternating long and short struts 29 and 31 so that the resulting zig-zag shape will form a helix 27 when disposed around a longitudinal axis. The helix may, however, be formed in other ways. For example, as seen in FIG. 6, all of the struts 629 forming the helix might be of the same length SL, while the hinge 637 might have legs 637a and 637b, of different lengths such that the resulting shape of the struts with the hinges with different length legs forms a helix.

FIG. 3 shows an embodiment of a helical stent 221 comprising two helical windings 227' and 227". The helical windings 227' and 227" comprise a plurality of pairs of long struts 229 and short struts 231 and a plurality of flexible hinge arrangements 261. In addition, the helical windings 227' and 227" comprise an additional strut 275 between two pairs of struts. The additional strut 275 is connected, via an additional hinge arrangement 261', at a first end 275a to an end 233 of a long strut 229 of a first strut pair and is connected, via a hinge arrangement 261, at a second end 275b to an end 235 of a short strut 231 of a second strut pair. The additional hinge arrangement 261' may be of a type similar to the hinge arrangement 261. The hinge arrangements 261 and 261' shown in FIG. 3 both comprise a substantially rigid connecting member 265 and 265' and a first and a second flexible hinge 267, 269 and 267' and 269' between the connecting member and the strut.

With reference to FIG. 3, it is, of course, not necessary that the struts 229 be longer than the struts 231 and a helical winding can, instead, comprise a plurality of pairs of long strut assemblies and short strut assemblies. The long strut assembly can comprise at least two struts 229 and 275 and can be longer than the short strut assembly, which can comprise one strut 231 or multiple struts, like the long strut assembly. The struts 229, 275, and 231 may all be the same length.

Figure 7:
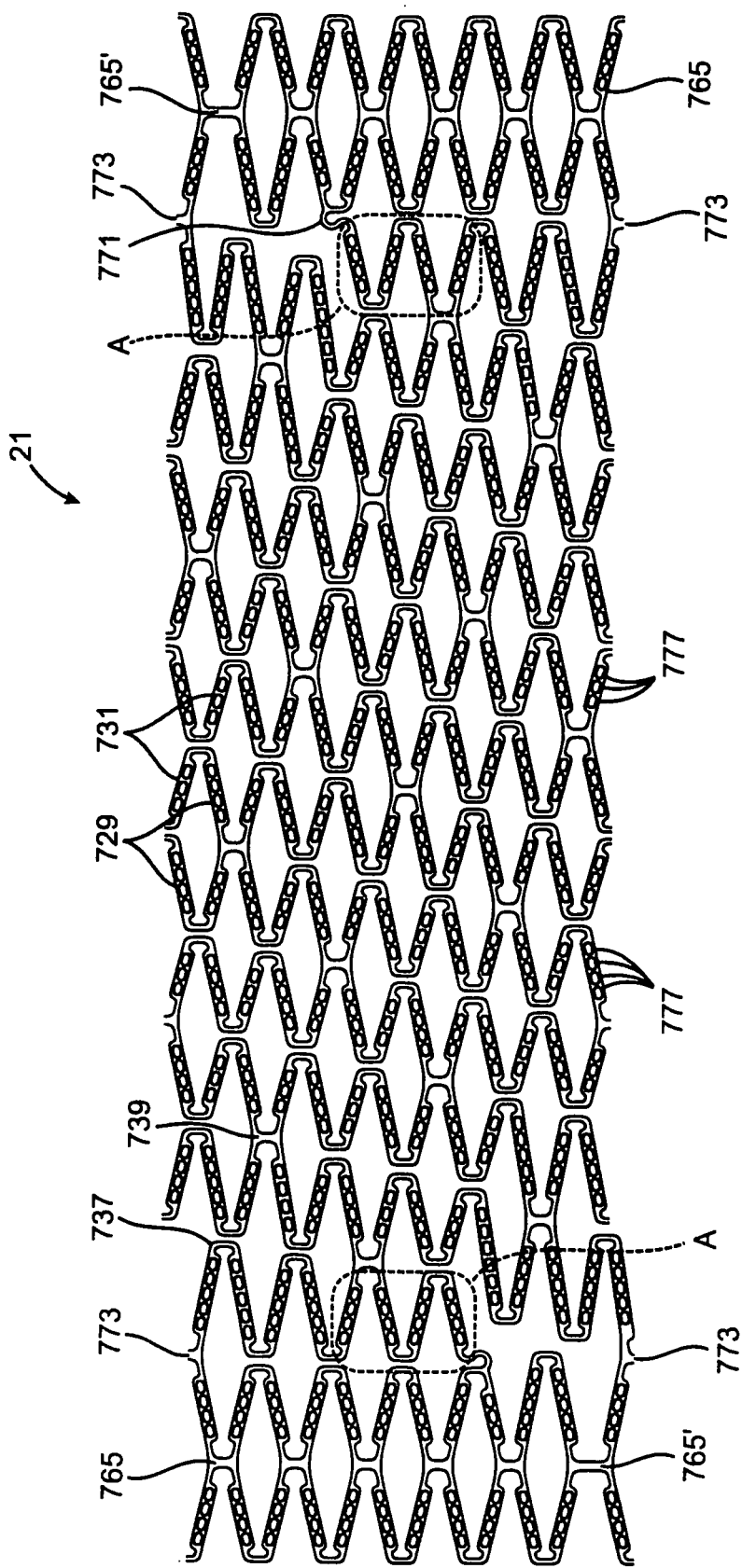
FIG. 7 is a view of a stent according to yet another embodiment of the present invention shown in partly expanded form, cut along a line parallel to a longitudinal axis of the stent, and unrolled.

FIG. 7 shows another embodiment of a stent 721 similar in many respects to the embodiment of the stent 21 shown in FIG. 1. Differences between the stent 721 and the stent 21 include that the stent 721 can comprise hinge arrangements 737 having a somewhat more recti-linear shape than the hinge arrangements 37 in the stent 21 in FIG. 1 which are curved or substantially semi-circular. In the stent 721, interconnection 739, end ring interconnection 765, and end interconnection 773 can be more compact to reduce spacing between windings than corresponding structures in the stent 21 of FIG. 1. Further, at least one end ring interconnection 765' can be elongated relative to other end ring elongated members 765 and can extend around a greater portion of the circumference of the stent. An end hinge arrangement 771 on the stent 721 can be longer and more curved, such as substantially S-shaped, than the end hinge arrangement 71 provided on the stent 21. On the stent 21, a majority of the long and short struts 29 and 31 have five and four drug receiving openings 77, respectively, a majority of the long and short struts 729 and 731 in the stent 721 can have four and three drug receiving openings 777, respectively. The features of the stent 721 including more squared hinge arrangements 737, thinner interconnections 739, 765, and 773, an elongated end ring interconnecting member 765', and a more elongated and curved end hinge arrangement 771 can facilitate, inter alia, flexibility of bending portions of the stent as well as improved uniformity upon expansion.

Figure 8:
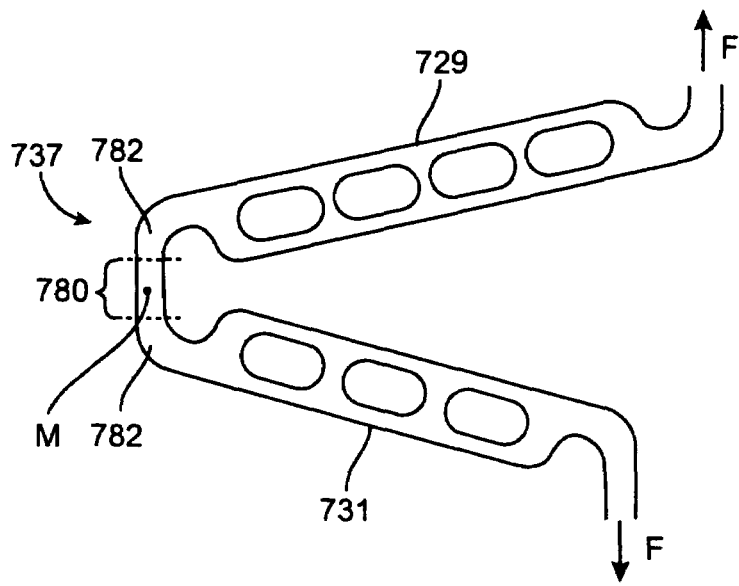
FIG. 8 is an enlarged view of one of the hinge arrangements from FIG. 7.

FIG. 8 shows one of the hinge arrangements 737 interconnecting a long strut 729 having four openings 777 with a short strut 731 having three openings. The hinge arrangements 737 of the embodiment of FIGS. 7 and 8 each have a straight active portion 780 which accommodates substantially all the bending during expansion of the stent. The active portion 780 is connected to the struts 729 and 731 by curved portions 782. The curved portions are not significantly deformed during expansion of the stent due to their slightly larger width than the active portion and due to their location in the hinge arrangement. Specifically, the forces applied to the struts due to stent expansion in the direction of the arrows F result in a highest moment applied at a location M on the hinge arrangement. A length of the active portion 780 of the hinge arrangement is selected to be long enough to provide acceptable peak strain while short enough to avoid excessive recoil. If the active portion of the hinge is very long, it will act like a spring. According to one preferred embodiment, the active portion 780 of the hinge has a length to width ratio of between 4:1 and 1:1, preferably about 2:1 and the hinge arrangement is straight over this length. By straight it is meant that both sides of the hinge arrangement are substantially straight in the as-cut configuration. This means that the straight hinges 780 will be slightly curved in the crimped (delivery) configuration and also curved in the expanded configuration.

Since the struts within the stent 721 are of differing lengths throughout the stent, the hinge arrangements 737 experience different moments applied by the different length struts. Thus, if the hinge arrangements were designed to be identical, the resulting expansion would be uneven. Some of the hinge arrangements 737 can be modified such as by changing the width or length of the active portion to achieve even expansion. For example, several locations within the stent 721 longer struts are used having five holes. These long five hole struts will exert a greater moment on the adjacent hinge arrangements due to their longer length than the three and four hole struts. Thus, the hinges adjacent the five hole struts can be wider and/or longer to achieve uniform expansion. This same principle applies anywhere there are variations in the lengths or shapes of the struts. To achieve a stent which opens evenly without certain hinges opening before others, the modified hinges are distributed in an uneven pattern on the stent which corresponds to the asymmetric structure of the stent.

Figure 9:
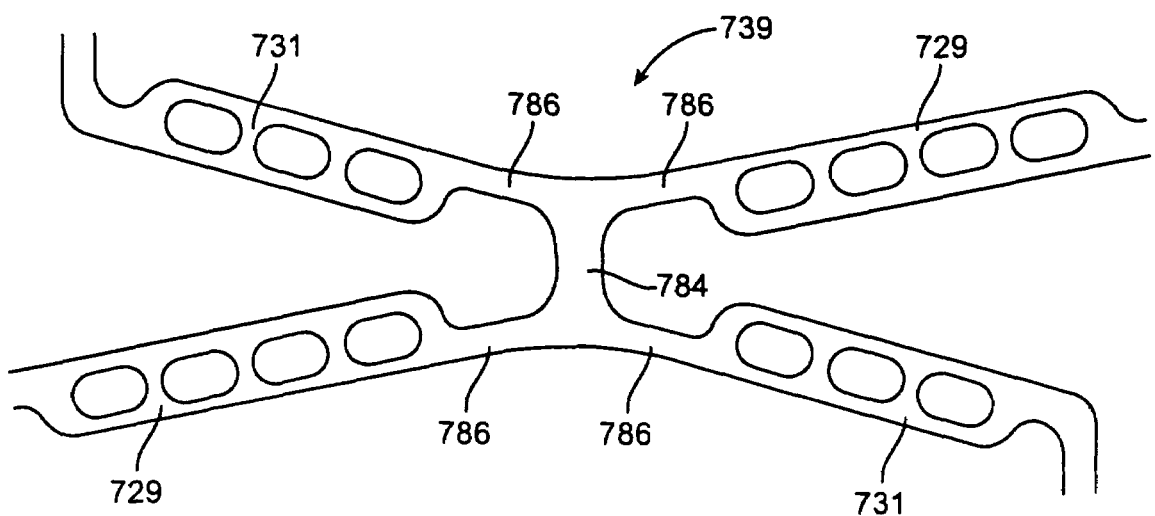
FIG. 9 is an enlarged view of one of the interconnection hinge arrangements from FIG. 7.

FIG. 9 shows one of the connection hinge arrangements 739 of the stent of FIG. 7. The connection hinge arrangements 739 each include a passive central portion 784 and four active tapered hinge portions 786 connecting to four struts 729 and 731. Each of the four active hinge portions 786 are tapered with a narrow end connected to the struts and a wider end connected to the passive central portion 784. This tapered configuration achieves a distribution of the maximum strain along the tapered hinge. This is in contrast to a straight hinge which would result in concentrated strain in the hinge at a location closest to the central portion. According to one preferred embodiment, the active tapered hinge portions 786 have a length to width ratio of between 5:1 and 1:1, preferably about 3:1 where the width measured is the smallest width of the tapered hinge.

Stents according to embodiments of the present invention will be provided in a variety of sizes to match the anatomy of the body lumens to be supported. Typical coronary stent lengths are about 8 to 38 mm; circumferences in the closed state are about 1 to 2 mm; and circumferences in the open state are about 2 to 6 mm. Although sizes for coronary stents are described, other types of stents may also be made according to the present invention and their size will depend on their use.

The length of a long strut in the embodiments described above is usually about 0.04" to 0.09" the length of a short strut is usually about 0.02" to 0.06"; the length of an end ring strut is usually about 0.02" to 0.09". The width of a long strut in the embodiments described above is usually about 0.005" to 0.01"; the width of a short strut is usually about 0.005" to 0.01"; the width of an end ring strut is usually about 0.005" to 0.01". The length of an interconnection hinge arrangement including four hinges is usually about 0.01" to 0.06", and its width at the central portion is usually about 0.005" to 0.02". The tubing from which the stent is laser cut, and thus the struts, hinge arrangements, interconnection hinge arrangements, and other features of the stent generally have a thickness which depends on the material used and for cobalt chromium alloys a thickness of about 0.004" to 0.006".

In the present application, the use of terms such as "including" is open-ended and is intended to have the same meaning as terms such as "comprising" and not preclude the presence of other structure, material, or acts. Similarly, though the use of terms such as "can" or "may" is intended to be open-ended and to reflect that structure, material, or acts are not necessary, the failure to use such terms is not intended to reflect that structure, material, or acts are essential. To the extent that structure, material, or acts are presently considered to be essential, they are identified as such.

While this invention has been illustrated and described in accordance with a preferred embodiment, it is recognized that variations and changes may be made therein without departing from the invention as set forth in the claims.

What is claimed is:

1. An expandable stent comprising:
   a plurality of struts extending in a substantially longitudinal direction along an axis of the stent in an unexpanded configuration; and
   a plurality of hinge arrangements interconnecting the struts, wherein each of the hinge arrangements includes a central portion and four tapered hinges, each central portion is connected to only the four tapered hinges and each one of the four tapered hinges is connected at one end to the central portion and at another end to a respective one of the plurality of struts and has a smallest width closer to its respective strut and a largest width closer to the central portion, and
   wherein each of the central portions extends in a substantially circumferential direction around the stent.

2. The stent of claim 1, wherein the four tapered hinges of the hinge arrangements are configured so that as the stent is expanded from the unexpanded configuration to an expanded configuration the four tapered hinges are deformed while the central portion and the struts are undeformed.

3. The stent of claim 1, wherein the struts include openings containing a beneficial agent, and wherein the openings are undeformed during expansion of the stent from the unexpanded configuration to an expanded configuration.

4. The stent of claim 1, wherein the plurality of struts include a plurality of short struts and a plurality of long struts positioned in an alternating arrangement, and wherein each of the plurality of hinge arrangements interconnects a combination of short and long struts.

5. The stent of claim 1, wherein the struts and hinge arrangements are interconnected to form a plurality of circumferential rings.

6. The stent of claim 1, wherein the struts and hinge arrangements are interconnected to form a plurality of helical windings.

7. The stent of claim 1, wherein the struts and hinge arrangements are interconnected to form a plurality of diamond shaped patterns.

8. The stent of claim 1, wherein the tapered hinges have a smallest width in the circumferential direction of the stent and the smallest widths of the plurality of hinges are varied to achieve uniform opening of the stent.

9. An expandable stent comprising:
   a plurality of struts extending in a substantially longitudinal direction along an axis of the stent in an unexpanded configuration;
   a plurality of first hinges interconnecting the struts, wherein the plurality of first hinges each have a straight active portion which extends in a substantially circumferential direction around the stent in the unexpanded configuration interconnected to adjacent ones of the plurality of struts; and
   a plurality of interconnecting hinge arrangements interconnecting the struts, wherein each of the interconnecting hinge arrangements includes a central portion and four second hinges each connected at one end to the central portion and at another end to one of the plurality of struts; and
   wherein each of the central portions extends substantially circumferentially around the stent.

10. The stent of claim 9, wherein the stent has a substantially helical wound structure formed from the struts.

11. The stent of claim 9, wherein the stent includes one or more circumferential rings formed from the struts.

12. The stent of claim 9, wherein the unexpanded configuration is an as cut configuration.

* * * * *